United States Patent
Fujita et al.

(10) Patent No.: US 9,504,768 B2
(45) Date of Patent: Nov. 29, 2016

(54) BIODEGRADABLE MATERIAL AND METHOD OF PRODUCING BIODEGRADABLE MATERIAL

(71) Applicant: Toray Industries, Inc., Tokyo (JP)

(72) Inventors: Masaki Fujita, Otsu (JP); Megumi Nakanishi, Otsu (JP); Kazuhiro Tanahashi, Otsu (JP)

(73) Assignee: Toray Industries, Inc. (JP)

( * ) Notice: Subject to any disclaimer, the term of this patent is extended or adjusted under 35 U.S.C. 154(b) by 177 days.

(21) Appl. No.: 14/387,718

(22) PCT Filed: Mar. 28, 2013

(86) PCT No.: PCT/JP2013/059210
§ 371 (c)(1),
(2) Date: Sep. 24, 2014

(87) PCT Pub. No.: WO2013/146999
PCT Pub. Date: Oct. 3, 2013

(65) Prior Publication Data
US 2015/0051355 A1 Feb. 19, 2015

(30) Foreign Application Priority Data
Mar. 28, 2012 (JP) .................. 2012-073777

(51) Int. Cl.
| | | |
|---|---|---|
| A61L 24/04 | (2006.01) | |
| A61L 15/26 | (2006.01) | |
| A61L 15/64 | (2006.01) | |
| A61L 24/00 | (2006.01) | |
| C08L 67/02 | (2006.01) | |
| C08L 67/04 | (2006.01) | |
| A61L 31/14 | (2006.01) | |
| C08L 101/16 | (2006.01) | |

(52) U.S. Cl.
CPC .............. *A61L 24/046* (2013.01); *A61L 15/26* (2013.01); *A61L 15/64* (2013.01); *A61L 24/0042* (2013.01); *A61L 31/148* (2013.01); *C08L 67/025* (2013.01); *C08L 67/04* (2013.01); *A61L 2400/04* (2013.01); *C08L 101/16* (2013.01)

(58) Field of Classification Search
None
See application file for complete search history.

(56) References Cited

U.S. PATENT DOCUMENTS

| | | | |
|---|---|---|---|
| 4,517,334 A | 5/1985 | Wilk et al. | |
| 5,093,319 A | 3/1992 | Higham et al. | |
| 5,202,352 A | 4/1993 | Okada et al. | |
| 5,225,521 A * | 7/1993 | Spinu ..................... C08G 63/08 | 525/415 |
| 5,612,052 A | 3/1997 | Shalaby | |
| 6,312,725 B1 * | 11/2001 | Wallace ................ A61L 24/043 | 424/484 |
| 6,387,391 B1 | 5/2002 | Shikinami et al. | |
| 2002/0010150 A1 | 1/2002 | Cortese et al. | |
| 2003/0108511 A1* | 6/2003 | Sawhney ......... A61B 17/00491 | 424/78.08 |
| 2006/0069168 A1 | 3/2006 | Tabata et al. | |
| 2006/0223975 A1 | 10/2006 | Tanaka et al. | |
| 2009/0117033 A1 | 5/2009 | O'Gara | |
| 2009/0311337 A1 | 12/2009 | Tanahashi et al. | |

FOREIGN PATENT DOCUMENTS

| | | |
|---|---|---|
| CN | 101240116 | 8/2008 |
| EP | 0 092 918 | 11/1983 |
| JP | 59-120658 | 7/1984 |
| JP | 5-969 | 1/1993 |
| JP | 5-17245 | 3/1993 |
| JP | 7-90041 | 10/1995 |
| JP | 2000-109666 | 4/2000 |
| JP | 3107514 | 9/2000 |
| JP | 2002-541923 | 12/2002 |
| JP | 2003-252936 | 9/2003 |
| JP | 2003-531682 | 10/2003 |
| JP | 3483753 | 10/2003 |
| JP | 2004-167229 | 6/2004 |
| JP | 2005-312623 | 11/2005 |
| JP | 2005-314535 | 11/2005 |
| JP | 2007-145826 | 6/2007 |
| JP | 2007-146146 | 6/2007 |
| JP | 2007-291323 | 11/2007 |
| JP | 2008-36134 | 2/2008 |
| JP | 4655505 | 1/2011 |
| JP | 4734772 | 5/2011 |
| JP | 4735260 | 5/2011 |
| WO | 96/21056 | 7/1996 |

OTHER PUBLICATIONS

Aldrich, Thermal Transistions of Homopolymers, Feb. 1, 2002.*
Chinese Office Action dated May 28, 2015, from corresponding Chinese Patent Application No. 201380016783.6.

* cited by examiner

*Primary Examiner* — Randy Gulakowski
*Assistant Examiner* — Christopher M Rodd
(74) *Attorney, Agent, or Firm* — DLA Piper LLP (US)

(57) ABSTRACT

A biodegradable material has an improved biodegradability, an enhanced shape recovery rate after deformation of the material and an improved flexibility. The biodegradable material is a chemically cross-linked product of: a multivalent compound A having 3 or more functional groups X such as hydroxyl group; a multivalent compound B having 3 or more functional groups Y such as carboxyl group; and a compound C having a structure originated from a hydroxycarboxylic acid whose homopolymer formed by homopolymerization has a glass transition point of −40° C. or lower.

14 Claims, No Drawings

US 9,504,768 B2

BIODEGRADABLE MATERIAL AND METHOD OF PRODUCING BIODEGRADABLE MATERIAL

TECHNICAL FIELD

This disclosure relates to a biodegradable material and a process of producing a biodegradable material.

BACKGROUND

For the purpose of hemostasis upon incision of an affected area, blocking the nutrient supply to a tumor, maintaining the concentration of an anticancer drug in a tumor, and the like, a poly(lactic acid/glycolic acid) copolymer (JP 5-969 A), a block copolymer of polyethylene glycol and polylactic acid etc. (JP 5-17245 B, JP 2004-167229 A, JP 2005-312623 A and JP 2007-291323 A), or a multi-block copolymer obtained by copolymerization of lactic acid, polyethylene glycol, polycarboxylic acid and the like (US 2009/0117033 A) is used as polymer particles for embolization of blood vessels and the like.

Such polymer particles for embolization of blood vessels and the like were associated with problems such as inability to achieve rapid biodegradation after having served their purpose. In addition, since these polymer particles, which are used in the form of spherical particles to tightly and securely embolize the blood vessels and the like, are delivered to a target site in a blood vessel or the like through a microcatheter with a small diameter or the like, there were problems such as an occurrence of clogging within the catheter due to insufficient flexibility of the polymer particles or aggregation between the particles, or irreversible deformation of the particles before their reaching to the target site.

To solve these problems, attempts to control the flexibility of polymer particles have been made, by developing polymer particles formed by blending several types of polymers (JP 2007-146146 A), or by developing chemically cross-linked polymer particles (JP 4655505 B). In addition, attempts such as coating the surface of the polymer particles with polyethylene glycol to prevent aggregation between polymer particles and to thereby improve their ability to pass through a catheter (JP 2007-145826 A) have also been reported.

Further, to prevent adhesion and the like between the damage to the surface of an organ which may occur due to surgery and the surrounding tissue, an in situ gel represented by a gel composed of a copolymer such as poly(ethylene glycol/polylactic acid), and poly glycolic acid and the like (JP 3107514 B), or a gel composed of dextran and poly N-isopropyl acrylamide (JP 2003-252936 A); or a binary gel represented by a gel composed of polyethylene glycol and the like and a polycarboxy polysaccharide (JP 2003-531682 A), a gel composed of 2 types of polyethylene glycols and the like (JP 2002-541923 A), or an ion-crosslinked gel such as carboxy methyl chitosan (JP 7-90041 B), for example, is used as a biodegradable material such as an anti-adhesive material, a wound dressing material, a hemostatic material or a urinary incontinence-preventing material.

A poly(ethylene glycol/propylene glycol) copolymer (WO 96/21056), a poly(lactic acid/dioxanone) copolymer (JP 3483753 B), a poly(ethylene glycol/modified amino acid/unmodified amino acid) copolymer (JP 4735260 B), a poly(lactic acid/depsipeptide/ethylene glycol) copolymer (JP 4734772 B), a porous sheet composed of a poly(lactic acid/ethylene glycol) copolymer (JP 2008-36134 A) or the like is also used as a biodegradable material such as an anti-adhesive material, a wound dressing material, a hemostatic material or a urinary incontinence-preventing material; and attempts to control the biodegradability and flexibility thereof have been made.

However, although improvement techniques such as blending several types of polymers (JP 2007-146146 A), use of chemically cross-linked polymer particles (JP 4655505 B), and coating the surface of polymer particles (JP 2007-145826 A) have served to improve the control of the flexibility of polymer particles or their ability to pass through a catheter, no sufficient improvement has been made regarding the problem of irreversible deformation of polymer particles. Further improvement was needed to provide suitable embolization effect for blood vessels and the like. Specifically, there was a need for the development of an embolization material for blood vessels and the like, such as polymer particles with a high capability to recover their original particle shapes after passing through a catheter (hereinafter referred to as "particle shape recovery rate").

Further, although improvements have been made in increasing biodegradability or flexibility of materials such as anti-adhesive materials, wound dressing materials, hemostatic materials or urinary incontinence-preventing materials, biodegradable materials composed of binary gels, for example, had a problem that their physical properties might be altered depending upon the environmental factors (such as temperature, humidity, or pH) or their blend ratio at the target site. In addition, since the organ or tissue surface damaged by surgery constantly keeps expanding and contracting, the biodegradable material located thereon may be deformed irreversibly. No sufficient improvements have been made regarding these problems of conventional biodegradable materials, and development of a material such as an anti-adhesive material, a wound dressing material, a hemostatic material or a urinary incontinence-preventing material having stable physical properties and a high shape recovery rate has been demanded.

Accordingly, it could be helpful to provide a biodegradable material having an enhanced shape recovery rate after deformation of the material and an improved flexibility.

SUMMARY

We thus provide the biodegradable material and the process of producing thereof as described in (1) to (16) below:

(1) A biodegradable material which is a chemically cross-linked product of: a multivalent compound A having 3 or more functional groups X selected from the group consisting of hydroxyl group, thiol group and amino group; a multivalent compound B having 3 or more functional groups Y selected from the group consisting of carboxyl group, isocyanate group and thioisocyanate group; and a compound C having a structure originated from a hydroxycarboxylic acid whose homopolymer formed by homopolymerization has a glass transition point of −40° C. or lower.

(2) The biodegradable material as described in (1) above, wherein the weight ratio of the structure originated from the compound C is 18 to 70% by weight.

(3) The biodegradable material as described in (1) or (2) above, wherein the multivalent compound A is one of the following a) to e):
    a) a homopolymer or a copolymer of a monomer(s) of a water-soluble polymer(s) selected from the group consisting of polyethylene glycol, polypropylene glycol, polyvinyl alcohol, polyhydroxyethyl acrylate, polyhydroxyethyl methacrylate, carboxymethyl cellulose, hydroxymethyl cellulose and hydroxyethyl cellulose;

b) a copolymer of the monomer of the water-soluble polymer and a monomer(s) of a hydrophobic polymer(s) selected from the group consisting of vinyl acetate and vinyl caprolactam;

c) a copolymer of the monomer of the water-soluble polymer and a hydroxycarboxylic acid(s) whose homopolymer(s) formed by homopolymerization has/have a glass transition point of −39° C. or higher;

d) a branched polymer formed by binding all of hydroxyl groups of a polyol with a homopolymer or a copolymer of a monomer(s) of a water-soluble polymer(s) selected from the group consisting of polyethylene glycol and polypropylene glycol;

e) a copolymer of the branched polymer and a hydroxycarboxylic acid(s) whose homopolymer(s) formed by homopolymerization has/have a glass transition point of −39° C. or higher.

4. The biodegradable material as described in any one of (1) to (3) above, wherein the multivalent compound B is one of the following f) to i):

f) a compound formed by binding a hydroxyl group(s) of a homopolymer or a copolymer of a monomer(s) of a water-soluble polymer(s) selected from the group consisting of polyethylene glycol, polypropylene glycol, polyvinyl alcohol, polyhydroxyethyl acrylate, polyhydroxyethyl methacrylate, carboxymethyl cellulose, hydroxymethyl cellulose and hydroxyethyl cellulose, with a polycarboxylic acid(s);

g) a compound formed by binding a hydroxyl group(s) of a copolymer of the monomer of the water-soluble polymer and a hydroxycarboxylic acid(s) whose homopolymer(s) formed by homopolymerization has/have a glass transition point of −39° C. or higher, with a polycarboxylic acid(s);

h) a compound formed by binding a hydroxyl group(s) of a branched polymer formed by binding all of hydroxyl groups of a polyol with a homopolymer or a copolymer of a monomer(s) of a water-soluble polymer(s) selected from the group consisting of polyethylene glycol and polypropylene glycol, with a polycarboxylic acid(s);

i) a compound formed by binding a hydroxyl group(s) of a copolymer of the branched polymer and a hydroxycarboxylic acid(s) whose homopolymer(s) formed by homopolymerization has/have a glass transition point of −39° C. or higher, with a polycarboxylic acid(s).

(5) The biodegradable material as described in any one of (1) to (4) above, wherein the compound C is a copolymer of a monomer(s) of a water-soluble polymer(s) selected from the group consisting of polyethylene glycol, polypropylene glycol, polyvinyl alcohol, polyhydroxyethyl acrylate, polyhydroxyethyl methacrylate, carboxymethyl cellulose, hydroxymethyl cellulose and hydroxyethyl cellulose, and a hydroxycarboxylic acid(s) whose homopolymer(s) formed by homopolymerization has/have a glass transition point of −40° C. or lower.

(6) The biodegradable material as described in any one of (1) to (5) above, wherein the compound C is 6-hydroxycaproic acid.

(7) The biodegradable material as described in any one of (3) to (6) above, wherein the branched polymer has a degree of branching of 3 to 16.

(8) The biodegradable material as described in any one of (3) to (7) above, wherein the polyol is selected from the group consisting of glycerin, polyglycerin and pentaerythritol.

(9) The biodegradable material as described in any one of (3) to (8) above, wherein the hydroxycarboxylic acid(s) whose homopolymer(s) formed by homopolymerization has/have a glass transition point of −39° C. or higher is/are selected from the group consisting of glycolic acid, lactic acid, glyceric acid, hydroxybutyric acid, malic acid, tartaric acid, hydroxyvaleric acid and 3-hydroxyhexanoic acid.

(10) The biodegradable material as described in any one of (4) to (9) above, wherein the polycarboxylic acid(s) is/are selected from the group consisting of oxalic acid, malonic acid, succinic acid, glutaric acid, adipic acid, pimelic acid, suberic acid, azelaic acid, sebacic acid, malic acid, tartaric acid and fumaric acid.

(11) A vascular embolization material composed of the biodegradable material as described in any one of (1) to (10) above.

(12) An anti-adhesive material composed of the biodegradable material as described in any one of (1) to (10) above.

(13) A wound dressing material composed of the biodegradable material as described in any one of (1) to (10) above.

(14) A hemostatic material composed of the biodegradable material as described in any one of (1) to (10) above.

(15) A urinary incontinence-preventing material composed of the biodegradable material as described in any one of (1) to (10) above.

(16) A process of producing a biodegradable material, the process comprising a cross-linking step wherein a multivalent compound A having 3 or more functional groups X selected from the group consisting of hydroxyl group, thiol group and amino group, a multivalent compound B having 3 or more functional groups Y selected from the group consisting of carboxyl group, isocyanate group and thioisocyanate group, and a compound C having a structure originated from a hydroxycarboxylic acid whose homopolymer formed by homopolymerization has a glass transition point of −40° C. or lower are dissolved in a solvent to allow chemical cross-linking reaction to proceed, to obtain the biodegradable material.

The biodegradable material has an improved biodegradability and an enhanced shape recovery rate after deformation of the material, and it can be suitably used as a vascular embolization material which, for example, can be easily delivered to a target site in a blood vessel or the like without clogging inside a catheter, and rapidly biodegrade and dissipate after having efficiently embolized the target site. Further, since the biodegradable material has an improved tensile and shear strength and is capable of recovering its shape after tensile or shear deformation, it can be suitably used as a material such as an anti-adhesive material, a wound dressing material, a hemostatic material or a urinary incontinence-preventing material, which is used, for example, pasted on an organ or surrounding tissue that constantly keeps expanding and contracting.

DETAILED DESCRIPTION

The terms used herein are as defined below unless otherwise specified.

The biodegradable material is characterized by being a chemically cross-linked product of: a multivalent compound A having 3 or more functional groups X selected from the group consisting of hydroxyl group, thiol group and amino group; a multivalent compound B having 3 or more functional groups Y selected from the group consisting of carboxyl group, isocyanate group and thioisocyanate group;

and a compound C having a structure originated from a hydroxycarboxylic acid whose homopolymer formed by homopolymerization has a glass transition point of −40° C. or lower.

The term "biodegradable" refers to a property of a biodegradable material to be degraded, dissolved, absorbed or metabolized in a living body or to be excreted from inside to the outside of the body. Examples of degradation reactions include hydrolysis and enzyme degradation. Hydrolysis is preferred because it does not depend on enzymes.

The term "chemical cross-linking" refers to binding of multivalent compound A, multivalent compound B and compound C using a cross-linker. Examples of bonds include ester bonds, thioester bonds, amide bonds and the like. Ester bonds are preferred because the biodegradability of the biodegradable material will be increased. The cross-linker is preferably a dehydration condensation agent. A state of being "chemically cross-linked" can be confirmed if no change in the appearance of the biodegradable material is observed after immersing the material in water at a temperature of 25° C. for 1 hour.

The weight ratio of the structure formed from the above compound C in the biodegradable material is preferably 18 to 70% by weight. To improve the flexibility and biodegradability of the resulting biodegradable material, the weight ratio is more preferably 20 to 65% by weight.

Examples of "multivalent compound A" include:

(i) a homopolymer or a copolymer of a monomer(s) of a water-soluble polymer(s) selected from the group consisting of polyethylene glycol (hereinafter referred to as "PEG"), polypropylene glycol (hereinafter referred to as "PPG"), polyvinyl alcohol (hereinafter referred to as "PVA"), polyhydroxyethyl acrylate, polyhydroxyethyl methacrylate, carboxymethyl cellulose, hydroxymethyl cellulose and hydroxyethyl cellulose;

(ii) a copolymer of the monomer of the water-soluble polymer and a monomer(s) of a hydrophobic polymer(s) selected from the group consisting of vinyl acetate and vinyl caprolactam;

(iii) a copolymer of the monomer of the water-soluble polymer and a hydroxycarboxylic acid(s) whose homopolymer(s) formed by homopolymerization has/have a glass transition point of −39° C. or higher;

(iv) a branched polymer formed by binding all of hydroxyl groups of a polyol with a homopolymer or a copolymer of a monomer(s) of a water-soluble polymer(s) selected from the group consisting of PEG and PPG; and (v) a copolymer of the branched polymer and a hydroxycarboxylic acid(s) whose homopolymer(s) formed by homopolymerization has/have a glass transition point of −39° C. or higher.

Multivalent compound A has 3 or more functional groups X selected from the group consisting of hydroxyl group, thiol group and amino group. Derivatives corresponding to multivalent compound A such as acid halides, esters, acid anhydrides and hydrochlorides are also included in multivalent compound A.

To achieve stable chemical cross-linking of multivalent compound A with multivalent compound B and compound C and to enhance the biocompatibility of the resulting biodegradable material, the "water soluble polymer" is preferably a polyalkylene glycol polymer such as PEG or PPG; a polyhydroxyalkyl (meth)acrylate polymer such as PVA, polyhydroxyethyl methacrylate or polyhydroxyethyl acrylate; or a cellulose polymer such as carboxymethyl cellulose, hydroxymethyl cellulose or hydroxyethyl cellulose; more preferably, a polyalkylene glycol polymer.

To improve the chemical cross-linking density of the resulting biodegradable material, multivalent compound A is preferably a branched compound such as a branched polymer (branched polymer a1) formed by binding all of hydroxyl groups of a polyol with a homopolymer or a copolymer of a monomer(s) of a water-soluble polymer(s) selected from the group consisting of PEG and PPG, more preferably a copolymer of the branched polymer and a hydroxycarboxylic acid(s) (hydroxycarboxylic acid a2), even more preferably, a block copolymer wherein the hydroxycarboxylic acid(s) is/are bound to the end(s) of the branched polymer. The polyol is preferably glycerin, polyglycerin or a monosaccharide such as pentaerythritol.

Examples of "multivalent compound B" include:

(i) a compound formed by binding a hydroxyl group(s) of a homopolymer or a copolymer of a monomer(s) of a water-soluble polymer(s) selected from the group consisting of PEG, PPG, PVA, polyhydroxyethyl acrylate, polyhydroxyethyl methacrylate, carboxymethyl cellulose, hydroxymethyl cellulose and hydroxyethyl cellulose, with a polycarboxylic acid(s);

(ii) a compound formed by binding a hydroxyl group(s) of a copolymer of the monomer of the water-soluble polymer and a hydroxycarboxylic acid(s) whose homopolymer(s) formed by homopolymerization has/have a glass transition point of −39° C. or higher, with a polycarboxylic acid(s);

(iii) a compound formed by binding a hydroxyl group(s) of a branched polymer formed by binding all of hydroxyl groups of a polyol with a homopolymer or a copolymer of a monomer(s) of a water-soluble polymer(s) selected from the group consisting of PEG and PPG, with a polycarboxylic acid(s); and (iv) a compound formed by binding a hydroxyl group(s) of a copolymer of the branched polymer and a hydroxycarboxylic acid(s) whose homopolymer(s) formed by homopolymerization has/have a glass transition point of −39° C. or higher, with a polycarboxylic acid(s).

Multivalent compound B has 3 or more functional groups Y selected from the group consisting of carboxyl group, isocyanate group and thioisocyanate group. Derivatives corresponding to multivalent compound B such as acid halides, esters and acid anhydrides are also included in multivalent compound B.

As the polycarboxylic acid, which is one of the components of multivalent compound B, a dicarboxylic acid such as oxalic acid, malonic acid, succinic acid, fumaric acid, glutaric acid, adipic acid, pimelic acid, suberic acid, azelaic acid, sebacic acid, malic acid, tartaric acid or dodecane dioic acid; or citric acid is preferred for their ease of availability. Succinic acid, which exists in a living body and is highly safe, is more preferred.

Multivalent compound B is preferably a branched compound such as a compound formed by binding a hydroxyl group(s) of a branched polymer (branched polymer b1) formed by binding all of hydroxyl groups of a polyol with a homopolymer or a copolymer of a monomer(s) of a water-soluble polymer(s) selected from the group consisting of PEG and PPG, with a polycarboxylic acid(s) (polycarboxylic acid b2). The polyol is preferably glycerin, polyglycerin or a monosaccharide such as pentaerythritol.

The "hydroxycarboxylic acid", which is one of the components of multivalent compound A, multivalent compound B and compound C, includes cyclic compounds such as cyclic dimers of hydroxycarboxylic acids. Derivatives of hydroxycarboxylic acids such as acid halides, esters and acid anhydrides are also included in the hydroxycarboxylic acid. As for a hydroxycarboxylic acid having optical isomers such as malic acid and tartaric acid, the hydroxycarboxylic acid includes all of its D-isomer, L-isomer, and mixtures thereof. Further, the hydroxycarboxylic acid includes copolymers formed by copolymerization of these hydroxycarboxylic acids. Examples of the hydroxycarboxylic acid include glycolic acid, lactic acid, glyceric acid, hydroxybutyric acid, malic acid, tartaric acid, hydroxyvaleric acid, 3-hydroxyhexanoic acid and 6-hydroxycaproic acid. Examples of the cyclic compound composed of hydroxycarboxylic acid include, glycolide which is a cyclic dimer of glycolic acid, lactide which is a cyclic dimer of lactic acid and ε-caprolactone which corresponds to 6-hydroxycaproic acid. Examples of the copolymer formed by copolymerization of hydroxycarboxylic acids include, copolymers of lactic acid and glycolic acid, copolymers of lactic acid and terephthalic acid, copolymers of lactic acid and isophthalic acid, copolymers of 6-hydroxycaproic acid and glycolic acid, and copolymers of 6-hydroxycaproic acid and polybutylene succinate (copolymers of 1,4-butanediol and succinic acid). The hydroxycarboxylic acid whose homopolymer formed by homopolymerization has a glass transition point of −39° C. or higher is preferably lactic acid.

Examples of the "hydroxycarboxylic acid whose homopolymer formed by homopolymerization has a glass transition point of −40° C. or lower", which is a component of "compound C", include 6-hydroxycaproic acid, copolymers of 6-hydroxycaproic acid and glycolic acid, and copolymers of 6-hydroxycaproic acid and polybutylene succinate (copolymers of 1,4-butanediol and succinic acid). 6-hydroxycaproic acid is preferred. The term "homopolymer" refers to a polymer formed by polymerization of a single type of monomers such as polylactic acid formed by polymerization of lactic acid alone. However, the "homopolymer formed by homopolymerization" in the present invention also encompasses polymers formed by polymerization of a single type of copolymers such as copolymers of lactic acid and glycolic acid.

To improve the chemical cross-linking density of compound C with multivalent compound A and multivalent compound B, the hydroxycarboxylic acid whose homopolymer formed by homopolymerization has a glass transition point of −40° C. or lower is preferably a copolymer of a monomer(s) of a water-soluble polymer(s) selected from the group consisting of PEG, PPG, PVA, polyhydroxyethyl acrylate, polyhydroxyethyl methacrylate, carboxymethyl cellulose, hydroxymethyl cellulose and hydroxyethyl cellulose, and a hydroxycarboxylic acid(s) whose homopolymer(s) formed by homopolymerization has/have a glass transition point of −40° C. or lower; more preferably, a copolymer of a branched polymer formed by binding all of hydroxyl groups of a polyol with a homopolymer or a copolymer of a monomer(s) of a water-soluble polymer(s) selected from the group consisting of PEG and PPG, and a hydroxycarboxylic acid(s) whose homopolymer(s) formed by homopolymerization has/have a glass transition point of −40° C. or lower.

When multivalent compound A, multivalent compound B and compound C are branched compounds, they preferably have a degree of branching of 3 to 16, more preferably 4 to 12. While too low a degree of branching results in a failure to improve the chemical cross-linking density and to provide sufficient strength of the biodegradable material, too high a degree of branching may hinder the chemical cross-linking reaction due to steric hindrance.

When multivalent compound A, multivalent compound B and compound C are copolymers, they may be any of a random copolymer, a block copolymer or an alternating copolymer. They are preferably a block copolymer, however, because the mechanical properties and the like of the resulting biodegradable material can be easily controlled and the flexibility and biodegradability thereof can be improved. The term "copolymer" herein refers to a high molecular compound formed by copolymerization of two or more types of monomers. The term "block copolymer", among these, refers to a copolymer in which at least two or more types of polymers composed of different repeating units are linked covalently to provide a molecular structure resembling a long chain, wherein the block refers to each of the "at least two or more types of polymers composed of different repeating units" constituting the block copolymer.

The weight ratio of the structure composed of the hydroxycarboxylic acid(s) whose homopolymer(s) formed by homopolymerization has/have a glass transition point of −39° C. or higher in the above mentioned multivalent compound A is preferably 10 to 300% by weight. To achieve an appropriate flexibility and biodegradability of the resulting biodegradable material, the weight ratio is more preferably 30 to 250% by weight, still more preferably 40 to 200% by weight.

The weight ratio of the structure composed of the hydroxycarboxylic acid(s) whose homopolymer(s) formed by homopolymerization has/have a glass transition point of −40° C. or lower in the above mentioned compound C is preferably 10 to 300% by weight. To achieve an appropriate flexibility and biodegradability of the resulting biodegradable material, the weight ratio is more preferably 30 to 250% by weight, still more preferably 40 to 200% by weight.

If the weight average molecular weights of multivalent compound A, multivalent compound B and compound C are too low, the biodegradation rate of the biodegradable material will be increased excessively, and a suitable embolization effect, for example, in vascular embolization application will not be obtained. On the other hand, if the weight average molecular weights of multivalent compound A, multivalent compound B and compound C are too high, biodegradability of the biodegradable material will be decreased. Therefore, the weight average molecular weights of the above multivalent compound A, multivalent compound B and compound C are preferably 1000 to 50000, more preferably 3000 to 30000. The weight average molecular weights of the above multivalent compound A, multivalent compound B and compound C can be measured by gel permeation chromatography (hereinafter referred to as "GPC method") under the following conditions.

Measurement Conditions

Apparatus (column): TSKgel GMHHR-M (manufactured by Tosoh Corporation; inner diameter: 7.8 mm; Length: 30 cm, two columns arranged linearly)

Eluent: chloroform

Column temperature: 35° C.

Flow velocity: 1.0 mL/min

Detection method: refractive index

Calibration curve: prepared using polystyrene standard samples

It is preferable that the value of NB/(NA+NC) is 1.2 to 4.0 when MB≥MAC, and the value of (NA+NC)/NB is 1.2 to 4.0 when MB<MAC, and these values are more preferably 1.3 to 3.0, still more preferably 1.4 to 2.5, wherein NA represents the number of moles of functional groups X contained in multivalent compound A; NB represents the number of moles of functional groups Y contained in multivalent compound B; and NC represents the number of moles of functional groups of compound C selected from the group consisting of hydroxyl group, thiol group, amino groups, carboxyl group, isocyanate group and thioisocyanate group; and wherein the variables below are defined as follows:

MA: the weight average molecular weight of multivalent compound A

MB: the weight average molecular weight of multivalent compound B

MC: the weight average molecular weight of compound C

MAC: the weight average molecular weight of the mixture of multivalent compound A and compound C.

According to the conventional technical knowledge (JP 2007-145826 A), equal amounts of NB and (NA+NC) will maximize the amount of the bond formed, i.e., maximize cross-linking density, theoretically, leaving no unreacted functional group. However, it is preferable that one of NB and (NA+NC) be used in excessive amount within the optimum range relative to the other.

The weight ratio and the like of a specific structure in each of multivalent compound A, multivalent compound B and compound C can be calculated based on the measurement results obtained by proton nuclear magnetic resonance method (hereinafter referred to as "$^1$H-NMR"), under the following conditions. For example, when the hydroxycarboxylic acid is lactic acid, the hydrogen atom of the methine group at the α-position is characteristic (chemical shift value: about 5.2 ppm). When the hydroxycarboxylic acid is 6-hydroxycaproic acid, the hydrogen atom of the methylene group at the α-position is characteristic (chemical shift value: about 2.3 ppm). When the hydroxycarboxylic acid is glycolic acid, the hydrogen atom of the methylene group at the α-position is characteristic (chemical shift value: about 4.8 ppm). With respect to PEG, on the other hand, the 4 hydrogen atoms of the ethylene group are characteristic (chemical shift value: about 3.5 ppm). Each weight ratio can be calculated based on the integral value of the signal appearing in each of these characteristic chemical shifts of the hydrogen atoms.

Measurement Conditions

Apparatus: JNM-EX270 (manufactured by JEOL Ltd., 270 MHz)

Solvent: deuterated chloroform (containing 0.05% by volume TMS as an internal standard)

Measurement temperature: 20° C.

When the biodegradable material of the present invention is obtained as an acetonitrile-containing film, the complex elastic modulus thereof is preferably from 40 to 400 kPa. The complex elastic modulus can be calculated based on the measurement results obtained by a viscoelasticity measuring apparatus (hereinafter referred to as a "rheometer") under the following conditions. Specifically, specified amounts of multivalent compound A, multivalent compound B and compound C (all as 0.3 g/mL acetonitrile solutions) as well as a catalyst (0.1 g/mL acetonitrile solution) and a stock solution of condensation agent are quickly mixed to provide a mixed solution. A 500 μL quantity of the mixed solution was then dropped onto the apparatus plate, inserting the mixed solution between the fixture and the apparatus plate, and the dynamic viscoelasticity test was performed 105 s after the compounding.

Measurement Conditions

Test name: dynamic viscoelasticity test

Apparatus: MCR301 (manufactured by Anton Parr Ltd.)

Fixture: CP40-1 (diameter: 39.958 mm; angle: 1°)

Gap: 0.081 mm (distance between the fixture and the apparatus plate between which the sample is inserted)

Strain: 0.1% (constant)

Angular frequency: 10 rad/s (constant)

Measurement temperature: 25° C.

Measurement time: 18000 s

The term "acetonitrile-containing film" refers to a film formed by chemically cross-linking multivalent compound A, multivalent compound B and compound C, with acetonitrile still contained, which film is obtained after the measurement by a rheometer.

The term "complex elastic modulus" is an index representing the flexibility of the biodegradable material, and refers to the value of the modulus E* (kPa) calculated by Equation 1 below, which value includes all of the elastic properties and the viscous properties of the sample to be measured, which is a viscoelastic body. Specifically, when the biodegradable material is used as a vascular embolization material, too low a value of the complex elastic modulus results in a failure to maintain the shape of the biodegradable material and to produce a desired embolization effect; whereas too high a value of the complex elastic modulus increases the resistance of the biodegradable material while passing through a catheter or the like. When the biodegradable material of the present invention is used as an anti-adhesive material, a wound dressing material, a hemostatic material, a urinary incontinence-preventing material or the like, too low a value of the complex elastic modulus results in a failure to maintain the shape of the biodegradable material and to produce a desired anti-adhesive effect on an organ or surrounding tissue; whereas too high a value of the complex elastic modulus causes an excessive load to the vibrational motion of the organ or surrounding tissue. Specifically, with respect to the biodegradable material, the complex elastic modulus of the acetonitrile-containing film at a constant strain of 0.1% and a constant angular frequency of 10 rad/s is preferably from 40 to 400 kPa, more preferably, from 100 to 300 kPa.

$$E^*=E'+iE'' \tag{1}$$

E': storage modulus (kPa)

E'': loss modulus (kPa)

i: imaginary unit

The term "storage modulus" herein refers to the component in phase with the applied strain (the real part of the complex elastic modulus), of the complex elastic modulus measured when the viscoelastic body is infinitesimally deformed at a constant strain and a constant angular frequency, and is an index representing the elastic properties of the sample to be measured. With respect to the biodegradable material, the storage modulus of the acetonitrile-containing film at a constant strain of 0.1% and a constant angular frequency of 10 rad/s is preferably 40 to 400 kPa, more preferably, 100 to 300 kPa. On the other hand, the term "loss modulus" refers to the component in opposite phase with the applied strain only by π/2 (the imaginary part of the complex elastic modulus), and is an index representing the viscous properties of the sample to be measured.

In the dynamic viscoelasticity test, gelation time, which is the time required for the biodegradable material to gel, can be evaluated relatively. The term "gelation time" refers to the time(s) required for the storage modulus and the loss modulus to reach the same value, i.e., time to reach a loss tangent of tan δ=1. The gelation time of the acetonitrile-containing film at a constant strain of 0.1% and a constant angular frequency of 10 rad/s is preferably 100 to 1000 s, more preferably 200 to 800 s. The "loss tangent" herein is an index representing the flexibility of the biodegradable material and the ability of the deformed acetonitrile-containing film to recover its original shape, and corresponds to the value, tan δ, calculated by Equation 2 below. Tan δ is a dimensionless value which represents the ability of the acetonitrile-containing film to absorb the energy applied when it is deformed, and to convert the energy to heat.

$$\tan \delta = E''/E' \qquad (2)$$

When the biodegradable material is obtained as a biodegradable film, the 50% compressive load of the film in the water-saturated state is an index representing the flexibility of the biodegradable material. The term "biodegradable film" herein refers to a film obtained by dissolving multivalent compound A, multivalent compound B and compound C in a solvent, and then by allowing chemical cross-linking reaction to proceed while removing the solvent.

The term "water-saturated state" refers to a state where, when approximately 20 mg of the biodegradable film was immersed in 10 mL of phosphate buffered saline at 37° C. (while a test tube as a container was rotated using a rotator at a rate of 0.5 rotation/second to shake the content), the water content of the biodegradable film has become constant. The expression "the water content is constant" refers to a state where, when the weight of the biodegradable film immersed in phosphate buffered saline at 37° C. was measured every minute, the rate of weight change with time thereof has become 10% or less. The rate of weight change with time is the value Rw (%) calculated by Equation 3 below.

$$Rw = \{W(t) - W(t-1)\}/W(t) \times 100 \qquad (3)$$

W(t): weight (g) of the biodegradable film after being immersed in water for t minutes W(t−1): weight (g) of the biodegradable film after being immersed in water for (t−1) minutes The term "water content" refers to the value Wr (%) calculated by Equation 4 below. The "biodegradable film in the dry state" herein refers to a film which was immersed in deionized water at 25° C. for 3 hours and then vacuum dried at 25° C. for 12 hours. The "biodegradable film in the water-saturated state" refers to a biodegradable film which was subjected to centrifugation (25° C., 1000 g×5 minutes) after its water content had become constant to remove phosphate buffered saline. The water content of the biodegradable film is increased by infiltration of water into the film. The higher the chemical cross-linking density of the biodegradable material, the more restricted the water infiltration into the biodegradable film becomes. Specifically, since there is a correlation between the water content and the chemical cross-linking density of the biodegradable material, the water content in the water-saturated state can be used as an index to determine the degree of chemical cross-linking $$Wr = (W - W0)/W \times 100 \qquad (4)$$

W: weight of the biodegradable film in the water-saturated state

W0: weight of the biodegradable film in the dry state (standard: about 20 mg)

The "50% compressive load" is an index representing the flexibility of the biodegradable material, and refers to a load required to compress a single biodegradable film to 50% of the original film thickness. While too low a value of the 50% compressive load results in a failure to maintain the shape of the biodegradable material, too high a value of the 50% compressive load causes problems such as an increase in the resistance of the material upon passing through a catheter. Therefore, with respect to the biodegradable material, the 50% compressive load of the biodegradable film in the water-saturated state is preferably 10 to 100 mN, more preferably 20 to 80 mN.

The 50% compressive load of the biodegradable film in the water-saturated state can be measured using a micro-strength evaluation tester, under the following conditions. Specifically, a load (changing) is applied to each biodegradable film described above to measure the load required to compress the film to 50% of the original film thickness.

Measurement Conditions
Test name: compression test
Apparatus: Micro Auto Model MST-I (manufactured by Shimadzu Corporation)
Measurement method: crosshead movement method
Measurement environment: room temperature, in an atmosphere
Specimen shape: 5 mm×5 mm
Specimen thickness: 1 mm
Specimen pretreatment: immersed in distilled water to the water-saturated state
Test rate: 0.1 mm/min
Upper pressurization factor: diameter 0.7 mm The term "recovery rate" refers to the ability of the biodegradable material released from compression to recover its original shape before the compression, for example, after passing through a catheter with a small inner diameter. Specifically, it is an index representing the recovery rate of the original shape. The recovery rate of the biodegradable film in the water-saturated state at a compression rate of 50% is preferably 70% or more, more preferably, 75% or more, because too low a recovery rate causes the biodegradable material to pass through the target site in the blood vessel to be embolized, for example, and to flow further downstream.

The recovery rate of the biodegradable film in the water-saturated state at a compression rate of 50% is measured using the same micro-strength evaluation tester as in the compression test under the following conditions, and corresponds to the value Rr (%) calculated by Equations 5 to 7 below. Specifically, a load (changing) is applied to the biodegradable film up to the 50% compressive load (i.e., the maximum test force, a compression rate of 50%) obtained by the compression test, and the load is then removed to the minimum test force.

Measurement Conditions
Test name: Load/load removal test
Apparatus: Micro Auto Model MST-I (manufactured by Shimadzu Corporation)
Measurement method: crosshead movement method
Measurement environment: room temperature, in an atmosphere
Specimen shape: 5 mm×5 mm
Specimen thickness: 1 mm
Specimen pretreatment: immersed in distilled water to the water-saturated state
Test rate: 0.1 mm/min
Upper pressurization factor: diameter 0.7 mm
Maximum test force: 50% compressive load of each film obtained in the
Compression Test
Minimum test force: 0.0001 N
End point after the load removal: 0.001 N
Load rate:
Load retention time:

$$L1 = L1b - L1a \qquad (5)$$

L1a: particle diameter change (μm) upon loading of the minimum test force

L1b: particle diameter change (μm) upon loading of the maximum test force $$L2 = L2b - L1a \quad (6)$$

L2b: particle diameter change (μm) upon loading of the maximum test force followed by removal of the load to the minimum test force $$Rr = \{(L1-L2)/L1\} \times 100 \quad (7)$$

The term "compression rate" refers to the ratio of the film thickness of the biodegradable film after compression to the original film thickness, and corresponds to the value Cr (%) calculated by Equation 8 below. The recovery rate refers to a recovery rate upon loading (changing) up to 50% compressive load, hence Cr=50(%).

$$Cr = (L1/d) \times 100 \quad (8)$$

d: average thickness of the biodegradable film (mm)

The biodegradable material is suitably used as a vascular embolization material. It is also suitably used as an anti-adhesive material, a wound dressing material, a hemostatic material, a urinary incontinence-preventing material or the like.

When the biodegradable material is used as a vascular embolization material, biodegradable particles can be used as they are, or used as a dispersion liquid in a suitable contrast medium or in a dispersion medium. Examples of the contrast medium include water-soluble contrast media such as iopamidol injection, ioxaglic acid injection and iohexol injection; and oily contrast media such as iodized poppy oil. Water-soluble contrast media are preferred. Examples of the dispersion medium include aqueous injection solutions and vegetable oils such as sesame oil and corn oil, containing a dispersant such as a polyoxysorbitan fatty acid ester, preservative such as methylparaben, or isotonic agent such as sodium chloride. The above mentioned vascular embolization material may further contain an antiseptic, stabilizer, solubilizer, excipient, and/or an effective component such as an antitumor agent.

Dr (%) is the residual weight ratio of the biodegradable material after immersing the film in phosphate buffered saline at 37° C. for a certain amount of time, and is calculated by Equation 9 below. The residual weight ratio after immersing the material for 30 days is preferably 5% or more, more preferably 50% or more, still more preferably 60% or more.

$$Dr = Dt/D0 \times 100 \quad (9)$$

Dt: weight of the biodegradable film after being immersed for a certain amount of time D0: weight of the biodegradable film before being immersed The process of producing a biodegradable material comprises a cross-linking step wherein a multivalent compound A having 3 or more functional groups X selected from the group consisting of hydroxyl group, thiol group and amino group, a multivalent compound B having 3 or more functional groups Y selected from the group consisting of carboxyl group, isocyanate group and thioisocyanate group, and a compound C having a structure originated from a hydroxycarboxylic acid whose homopolymer formed by homopolymerization has a glass transition point of −40° C. or lower are dissolved in a solvent to allow chemical cross-linking reaction to proceed, to obtain the biodegradable material.

Examples of multivalent compound A include a block copolymer of branched polymer a1 formed by binding all of hydroxyl groups of a polyol with PEG and PPG, and hydroxycarboxylic acid a2 (herein after referred to as "hydroxycarboxylic acid a2") whose homopolymer formed by homopolymerization has a glass transition point of −39° C. or higher. Examples of branched polymer a1 include 4-branched PEG (PTE series; manufactured by NiGK Corporation) and 8-branched PEG (HGEO series; manufactured by NiGK Corporation).

When hydroxycarboxylic acid a2 is lactic acid, glycolic acid or the like, condensation polymerization is preferred as the process of producing multivalent compound A, which is a block copolymer of branched polymer a1 and hydroxycarboxylic acid a2. When hydroxycarboxylic acid a2 is a cyclic compound such as lactide or glycolide, ring-opening polymerization is preferred.

As the reaction solvent for the condensation polymerization, a good solvent for branched polymer a1 such as 4-branched PEG or 8-branched PEG and hydroxycarboxylic acid a2 is used. Examples include dichloromethane, chloroform, acetonitrile and tetrahydrofuran, and mixed solvents thereof. The reaction temperature is preferably set such that the good solvent employed refluxes. The reaction pressure may be a reduced pressure, but normal pressure is preferred for ease of operation. The reaction time is preferably 2 to 48 hours, more preferably 4 to 24 hours, in order to appropriately control the molecular weight of the resulting multivalent compound A.

The total concentration of branched polymer a1 and hydroxycarboxylic acid a2 in the condensation polymerization varies depending on the types and the like of a1 and a2 used, and is preferably 10 to 100% by weight, more preferably 50 to 100% by weight. The concentration of the catalyst in the reaction solvent is preferably 0.01 to 0.5% by weight, more preferably 0.1 to 0.3% by weight, since too high a concentration complicates the removal of the catalyst after the reaction while too low a concentration hinders the reaction.

As the reaction solvent for the ring-opening polymerization, the same good solvent as for the condensation polymerization may be used. To increase the reactivity, however, it is preferable not to use the reaction solvent and to set the reaction temperature to 90° C. to 150° C., more preferably to 100° C. to 130° C. The reaction pressure may be a reduced pressure, but normal pressure is preferred for ease of operation. The reaction time is preferably 2 to 48 hours, more preferably 4 to 24 hours, in order to appropriately control the molecular weight of the resulting multivalent compound A.

Examples of the catalyst include metal catalysts. Examples of the metal catalyst include metal alkoxides, metal halides, organic carboxylic acid salts, carbonic acid salts, sulfuric acid salts and oxides of tin, titanium, lead, zinc, cobalt, iron, lithium or a rare earth. In terms of polymerization reactivity, tin compounds are preferred. Examples of the tin compound include tin powder, tin(II) chloride, tin(IV) chloride, tin(II) bromide, tin(IV) bromide, ethoxytin(II), t-butoxytin(IV), isopropoxytin(IV), tin(II) acetate, tin(IV) acetate, tin(II) octylate, tin(II) laurate, tin(II) myristate, tin(II) palmitate, tin(II) stearate, tin(II) oleate, tin(II) linoleate, tin(II) acetylacetonate, tin(II) oxalate, tin(II) lactate, tin(II) tartrate, tin(II) pyrophosphate, tin(II) p-phenolsulfonate, tin(II) bis(methanesulfonate), tin(II) sulfate, tin(II) oxide, tin(IV) oxide, tin(II) sulfide, tin(IV) sulfide, dimethyltin(IV) oxide, methylphenyltin(IV) oxide, dibutyltin(IV) oxide, dioctyltin(IV) oxide, diphenyltin(IV) oxide, tributyltin oxide, triethyltin(IV) hydroxide, triphenyltin(IV)

hydroxide, tributyltin hydride, monobutyltin(IV) oxide, tetramethyltin(IV), tetraethyltin(IV), tetrabutyltin(IV), dibutyldiphenyltin(IV), tetraphenyltin(IV), tributyltin(IV) acetate, triisobutyltin(IV) acetate, triphenyltin(IV) acetate, dibutyltin diacetate, dibutyltin dioctoate, dibutyltin(IV) dilaurate, dibutyltin(IV) maleate, dibutyltin bis(acetylacetonate), tributyltin(IV) chloride, dibutyltin dichloride, monobutyltin trichloride, dioctyltin dichloride, triphenyltin (IV) chloride, tributyltin sulfide, tributyltin sulfate, tin(II) methanesulfonate, tin(II) ethanesulfonate, tin(II) trifluoromethanesulfonate, ammonium hexachlorostannate(IV), dibutyltin sulfide, diphenyltin sulfide, triethyltin sulfate and tin(II) phthalocyanine. The catalyst for the condensation polymerization is preferably tin(II) oxide, and the catalyst for the ring-opening polymerization is preferably tin(II) octylate.

Examples of multivalent compound B include a branched compound formed by binding a branched polymer b1 formed by binding all of hydroxyl groups of a polyol with PEG or PPG, with a polycarboxylic acid b2. Examples of branched polymer b1 include 4-branched PEG and 8-branched PEG.

As the process of producing multivalent compound B formed by binding branched polymer b1 with polycarboxylic acid b2, condensation reaction using a dehydration condensation agent is preferred. Alternatively, polycarboxylic acid a2 may first be reacted with an electrophilic halogenating agent such as thionyl chloride or oxalyl chloride to be converted to a derivative such as an acid halide, acid anhydride or ester, which may then be subjected to condensation reaction to provide multivalent compound B.

Examples of the dehydration condensation agent include carbodiimide compounds such as N,N'-dicyclohexylcarbodiimide, N,N'-diisopropylcarbodiimide, 1-ethyl-3-(3-dimethylaminopropyl)carbodiimide, 1-ethyl-3-(3-dimethylaminopropyl)carbodiimide hydrochloride (hereinafter referred to as "EDC"), 1,3-bis(2,2-dimethyl-1,3-dioxolane-4-ylmethyl)carbodiimide, N-{3-(dimethylamino)propyl-}-N'-ethylcarbodiimide, N-{3-(dimethylamino)propyl-}-N'-ethylcarbodiimide methiodide, N-tert-butyl-N'-ethylcarbodiimide, N-cyclohexyl-N'-(2-morpholinoethyl)carbodiimide meso-p-toluene sulfonate, N,N'-di-tert-butyl carbodiimide and N,N'-di-p-tricarbodiimide. EDC is preferred for ease of treatment of the reaction side product.

The dehydration condensation agent may be used with a dehydration condensation accelerator. Examples of the dehydration condensation accelerator include pyridine, 4-dimethylamino pyridine (hereinafter referred to as "DMAP"), triethylamine, isopropyl amine, 1-hydroxybenzotriazol and N-hydroxysuccinic acid imide.

As the reaction solvent for the condensation reaction of branched polymer b1 and polycarboxylic acid b2, a good solvent for b1 and b2 is used. Examples include dichloromethane, chloroform, acetonitrile and tetrahydrofuran, and mixed solvents thereof. The reaction temperature is preferably set such that the good solvent employed refluxes. The reaction pressure may be a reduced pressure, but normal pressure is preferred for ease of operation. The reaction time is preferably 2 to 48 hours, more preferably 4 to 24 hours, in order to appropriately control the molecular weight of the resulting multivalent compound B.

The total concentration of branched polymer b1 and polycarboxylic acid b2 in the condensation reaction varies depending on the types and the like of b1 and b2 used, and is preferably 10 to 100% by weight, more preferably 20 to 80% by weight. The concentration of the catalyst in the reaction solvent is preferably 0.01 to 0.5% by weight, more preferably 0.1 to 0.3% by weight, since too high a concentration complicates the removal of the catalyst after the reaction while too low a concentration hinders the reaction.

Examples of the catalyst include pyridine, DMAP, triethylamine and isopropyl amine. Pyridine is preferred for ease of removal.

As compound C, for example, a branched block copolymer (hereinafter referred to as "block copolymer C") of polymer c1 formed by binding all of hydroxyl groups of a polyol with PEG and PPG, and hydroxycarboxylic acid c2 (hereinafter referred to as "hydroxycarboxylic acid c2") whose homopolymer formed by homopolymerization has a glass transition point of −40° C. or lower, is even more preferred.

When hydroxycarboxylic acid c2 is 6-hydroxycaproic acid and the like, condensation polymerization is preferred as the process of producing block copolymer C, which is formed by copolymerization of branched polymer c1 and hydroxycarboxylic acid c2. When hydroxycarboxylic acid c2 is a cyclic compound such as ε-caprolactone and the like, ring-opening polymerization is preferred.

As the reaction solvent for the condensation polymerization, a good solvent for branched polymer c1 such as 4-branched PEG or 8-branched PEG and hydroxycarboxylic acid c2 is used. Examples include dichloromethane, chloroform, acetonitrile and tetrahydrofuran, and mixed solvents thereof. The reaction temperature is preferably set such that the good solvent employed refluxes. The reaction pressure may be a reduced pressure, but normal pressure is preferred for ease of operation. The reaction time is preferably 2 to 48 hours, more preferably 4 to 24 hours, in order to appropriately control the molecular weight of the resulting compound C.

The total concentration of branched polymer c1 and hydroxycarboxylic acid c2 in the condensation polymerization varies depending on the types and the like of c1 and c2 used. It is preferably 10 to 100% by weight, more preferably 50 to 100% by weight. The concentration of the catalyst in the reaction solvent is preferably 0.01 to 0.5% by weight, more preferably 0.1 to 0.3% by weight, since too high a concentration complicates the removal of the catalyst after the reaction while too low a concentration hinders the reaction.

As the reaction solvent for the ring-opening polymerization, the same good solvent as for the condensation polymerization may be used. To increase the reactivity, however, it is preferable not to use the reaction solvent and to set the reaction temperature to 90° C. to 150° C., more preferably to 100° C. to 130° C. The reaction pressure may be a reduced pressure, but normal pressure is preferred for ease of operation. The reaction time is preferably 2 to 48 hours, more preferably 4 to 24 hours to appropriately control the molecular weight of the resulting compound C.

Examples of the catalyst include the same metal catalysts as used for the production of multivalent compound A.

Although the obtained multivalent compound A, multivalent compound B and compound C may be used in the chemical cross-linking step without purification, they may be purified to remove unreacted materials, the solvent and the catalyst. Examples of such methods for purification include fractional precipitation.

The fractional precipitation is a method in which obtained multivalent compound A, multivalent compound B or compound C is dissolved in a good solvent, and the resulting solution is added dropwise to a poor solvent under stirring to obtain purified multivalent compound A, multivalent compound B or compound C as a precipitate. The term "good solvent" herein refers to an organic solvent in which the above multivalent compound A, multivalent compound B or compound C can be dissolved, whereas the term "poor solvent" refers to an organic solvent in which the above multivalent compound A, multivalent compound B or compound C cannot be dissolved.

Examples of the good solvent used in the fractional precipitation include dichloromethane, chloroform, acetonitrile and tetrahydrofuran, and mixed solvents thereof. The amount of the good solvent used varies depending on the composition and the like of the obtained multivalent compound A, multivalent compound B or compound C, and the concentration of the dissolved multivalent compound A, multivalent compound B or compound C is preferably 10 to 80% by weight, more preferably 20 to 70% by weight. Examples of the poor solvent used in the fractional precipitation include alcohol organic solvents such as methanol and ethanol; ether organic solvents such as dimethyl ether, ethyl methyl ether and diethyl ether; hydrocarbon organic solvents such as pentane, hexane, heptane and octane; and mixed solvents thereof. The amount of the poor solvent used also varies depending on the composition and the like of the obtained multivalent compound A, multivalent compound B or compound C. It is preferably 50 to 1000% by weight, more preferably 100 to 500% by weight relative to the good solvent. In terms of controlling the molecular weight distribution, a process is preferred in which multivalent compound A, multivalent compound B or compound C is dissolved in dichloromethane and the resulting solution is added dropwise to diethyl ether under stirring. Further, to enhance the purity of the purified product, the obtained purified product is preferably washed with a poor solvent, more preferably, washed 2 to 5 times.

In a chemical cross-linking step in which multivalent compound A, multivalent compound B and compound C are dissolved in a solvent and chemical cross-linking reaction is allowed to proceed to obtain the biodegradable material, use of a protic solvent such as water or alcohol is not preferable, because the protic solvent itself may be involved in the chemical cross-linking step and the chemical cross-linking density of the resulting biodegradable material may be significantly reduced. As the solvent used in the chemical cross-linking step, an aprotic polar organic solvent with a dielectric constant of 35 to 50 is preferred.

As the aprotic polar organic solvent with a dielectric constant of 35 to 50, N,N-dimethylformamide (hereinafter referred to as "DMF"), N,N-dimethyl acetamide, acetonitrile or dimethylsulfoxide (hereinafter referred to as "DMSO") is preferred. Acetonitrile is more preferred for ease of removal by evaporation under reduced pressure.

A dehydration condensation agent may be used in the chemical cross-linking step. Examples of the dehydration condensation agent used in the chemical cross-linking step include carbodiimide compounds such as N,N'-dicyclohexylcarbodiimide, N,N'-diisopropylcarbodiimide, EDC, N-{3-(dimethylamino)propyl-}-N'-ethylcarbodiimide, N-{3-(dimethylamino)propyl-}-N'-ethylcarbodiimide methiodide, N-tert-butyl-N'-ethylcarbodiimide, N-cyclohexyl-N'-(2-morpholinoethyl)carbodiimide meso-p-toluene sulfonate, N,N'-di-tert-butyl carbodiimide and N,N'-di-p-tricarbodiimide. EDC is preferred for ease of treatment of the reaction side product.

The dehydration condensation agent may be used with a dehydration condensation accelerator. Examples of the dehydration condensation accelerator include pyridine, DMAP, triethylamine, isopropyl amine, 1-hydroxybenzotriazole, N-hydroxysuccinic acid imide and the like. DMAP is preferred for high reactivity and ease of removal after reaction.

Examples of the process of producing the biodegradable material as a biodegradable film include a process in which multivalent compound A, multivalent compound B and compound C dissolved in an aprotic polar organic solvent with a dielectric constant of 35 to 50 are introduced in a poor solvent, and chemical cross-linking reaction is then allowed to proceed while removing the aprotic polar organic solvent.

Preferable examples of the poor solvent used to obtain the biodegradable film include oils such as synthetic oils and natural oils. Natural oils are more preferred.

Examples of the synthetic oil include silicone oils. Examples of the natural oil include cottonseed oil, corn oil, coconut oil, olive oil, palm oil, rapeseed oil, safflower oil, sesame oil, soybean oil, sunflower oil, turpentine oil, almond oil, avocado oil, bergamot oil, castor oil, cedar oil, chlorophyll oil, clove oil, croton oil, eucalyptus oil, fennel oil, fusel oil, grape seed oil, jojoba oil, kukui nut oil, lavender oil, lemon oil, linseed oil, macadamia nut oil, meadowfoam oil, orange oil, origanum oil, persic oil and rose hip oil. Cottonseed oil, corn oil, olive oil, rapeseed oil, safflower oil, sesame oil, soybean oil, or sunflower oil is preferred for its high biological safety and stable availability.

EXAMPLES

Our materials and methods will now be described in detail with reference to Examples and Comparative Examples, but it should be understood that this disclosure is not construed as being limited thereto.

Example 1

In an eggplant flask, 10.0 g of 8-branched PEG (SUNBRIGHT (registered trademark) HGEO5000; manufactured by NiGK Corporation) as branched polymer a1, and 22.0 g of lactide (PURASORB L; manufactured by Purac Biomaterials) as hydroxycarboxylic acid a2 were placed. These were melt mixed under an argon atmosphere at 120° C., and then 0.94 mL of a solution of tin(II) octylate (tin(II) octylate (manufactured by Sigma-Aldrich Co.,) dissolved in toluene (manufactured by Wako Pure Chemical Industries, Ltd.) and adjusted to a concentration of 0.16 g/mL) as a catalyst was added to the resulting mixture, followed by copolymerization reaction for 20 hours at normal pressure to obtain crude multivalent compound A1.

The obtained crude multivalent compound A1 was added dropwise to 100 mL of diethyl ether, and the resulting precipitate and the liquid component separating from diethyl ether were collected. These were then washed three times with 50 mL of diethyl ether to give purified multivalent compound A1. The weight average molecular weight of the purified multivalent compound A1 as measured by GPC method was 15,400.

In an eggplant flask, 10.0 g of 8-branched PEG (SUNBRIGHT (registered trademark) HGEO5000; manufactured by NiGK Corporation) as branched polymer b1, and 3.2 g of anhydrous succinic acid (manufactured by Wako Pure Chemical Industries, Ltd.) as polycarboxylic acid b2 were placed. To the flask, 1 mL of dehydrated pyridine (manufactured by Wako Pure Chemical Industries, Ltd.) as a catalyst, and 40 mL of dehydrated chloroform solution (manufactured by Wako Pure Chemical Industries, Ltd.) as a solvent were added, and the mixture was heated to 80° C., followed by reaction at normal pressure for 24 hours to give crude multivalent compound B1.

The obtained multivalent compound B1 was added dropwise to 100 mL of diethyl ether, and the resulting precipitate and the liquid component separating from diethyl ether were collected. These were then washed three times with 50 mL of diethyl ether to give purified multivalent compound B1. The weight average molecular weight of the purified multivalent compound B1 as measured by GPC method was 5,800.

In an eggplant flask, 10.0 g of 8-branched PEG (SUNBRIGHT® HGEO5000; manufactured by NiGK Corporation) as branched polymer c1 and 20.0 g of ε-caprolactone (manufactured by Wako Pure Chemical Industries, Ltd.) as hydroxycarboxylic acid c2 were placed. These were melt mixed under an argon atmosphere at 120° C., and then 0.94 mL of a solution of tin(II) octylate (tin(II) octylate (manufactured by Sigma-Aldrich Co.,) dissolved in toluene (manufactured by Wako Pure Chemical Industries, Ltd.) and adjusted to a concentration of 0.16 g/mL) as a catalyst was added to the resulting mixture, followed by copolymerization reaction for 20 hours at normal pressure to obtain crude compound C3. The weight average molecular weight of the purified compound C1 as measured by GPC method was 13,600.

The obtained compound C1 was added dropwise to 100 mL of diethyl ether, and the resulting precipitate and liquid component separating from diethyl ether were collected. These were then washed three times with 50 mL of diethyl ether to give purified compound C3. The weight average molecular weight of the purified compound C3 as measured by GPC method was 13,600.

The obtained purified multivalent compound A1, purified multivalent compound B1 and purified compound C1 were dried under reduced pressure, and each of these were dissolved in dehydrated acetonitrile (manufactured by Wako Pure Chemical Industries, Ltd.) to a concentration of 0.3 g/mL, respectively, to obtain solutions 1, 2 and 3. Into a mold composed of a 1 mm thick glass plate, 0.295 mL of solution 1, 0.444 mL of solution 2, 0.261 mL of solution 3, 0.022 mL of DMAP/acetonitrile solution (0.1 g/mL) as a catalyst, and 0.039 mL of EDC stock solution as a condensation agent were poured, and acetonitrile was removed by immersing the mold in cottonseed oil warmed to 55° C. to obtain biodegradable film 1.

The biodegradability test was performed to calculate the residual weight ratio of the obtained biodegradable film 1. The compressive load and the recovery rate of the film were also measured. The results are shown in Table 1.

Further, solutions 1-3, DMAP/acetonitrile solution, and EDC stock solution, having the same concentration as the above-described biodegradable film 1 were mixed at the same volume ratio to obtain acetonitrile-containing film 1.

The dynamic viscoelasticity test was performed to measure the complex elastic modulus of the obtained acetonitrile-containing film 1. The results are shown in Table 1.

As shown in Table 1, biodegradable film 1 had a high residual weight ratio, a high compressive load, and a high recovery rate. Acetonitrile-containing film 1 had a high complex elastic modulus.

Example 2

The same operation as in Example 1 was carried out except that the amount of solution 1 was changed to 0.199 mL, the amount of solution 2 was changed to 0.450 mL, the amount of solution 3 was changed to 0.351 mL, the amount of DMAP solution was changed to 0.023 mL, and the amount of EDC was changed to 0.040 mL, to obtain biodegradable film 2 and acetonitrile-containing film 2.

Biodegradable film 2 and acetonitrile-containing film 2 were evaluated in the same manner as in Example 1. The results are shown in Table 1.

As shown in Table 1, biodegradable film 2 had a high residual weight ratio, a high compressive load, and a high recovery rate. Acetonitrile-containing film 2 had a high complex elastic modulus.

Example 3

The same operation as in Example 1 was carried out except that 8-branched PEG (SUNBRIGHT (registered trademark) HGEO5000; manufactured by NiGK Corporation) was used instead of multivalent compound A1 to obtain solution 4. The weight average molecular weight of the 8-branched PEG (SUNBRIGHT (registered trademark) HGEO5000; manufactured by NiGK Corporation) as measured by GPC method was 5,000.

The same operation as in Example 1 was carried out except that 0.295 mL of solution 1 was changed to 0.120 mL of solution 4, the amount of solution 2 was changed to 0.555 mL, the amount of solution 3 was changed to 0.325 mL, the amount of DMAP solution was changed to 0.028 mL, the amount of EDC was changed to 0.049 mL, to obtain biodegradable film 3 and acetonitrile-containing film 3.

Biodegradable film 3 and acetonitrile-containing film 3 were evaluated in the same manner as in Example 1. The results are shown in Table 1.

As shown in Table 1, biodegradable film 3 had a high residual weight ratio, a high compressive load, and a high recovery rate. Acetonitrile-containing film 3 had a high complex elastic modulus.

Example 4

The same operation as in Example 1 was carried out except that 10.0 g of branched polymer a1 was changed to 8-branched PEG (SUNBRIGHT (registered trademark) HGEO10000; manufactured by NiGK Corporation) to obtain purified multivalent compound A2. The weight average molecular weight of the purified multivalent compound A2 as measured by GPC method was 18,600. The same operation as in Example 1 was carried out except that 10.0 g of branched polymer b1 was changed to 8-branched PEG (SUNBRIGHT (registered trademark) HGEO10000; manufactured by NiGK Corporation) to obtain purified multivalent compound B2. The weight average molecular weight of the purified multivalent compound B2 as measured by GPC method was 10,800. The same operation as in Example 1 was carried out except that 10.0 g of branched polymer c1 was changed to 8-branched PEG (SUNBRIGHT (registered trademark) HGEO10000; manufactured by NiGK Corporation) to obtain purified compound C2. The weight average molecular weight of the purified compound C2 as measured by GPC method was 21,700.

The same operation as in Example 1 was carried out except that purified multivalent compound A1 was changed to purified multivalent compound A2 to obtain solution 5. The same operation as in Example 1 was carried out except that purified multivalent compound B1 was changed to purified multivalent compound B2 to obtain solution 6. The same operation as in Example 1 was carried out except that purified compound C1 was changed to purified compound C2 to obtain solution 7.

The same operation as in Example 1 was carried out except that 0.295 mL of solution 1 was changed to 0.418 mL of solution 5, 0.444 mL of solution 2 was changed to 0.534 mL of solution 6, 0.261 mL of solution 3 was changed to 0.049 mL of solution 7, the amount of DMAP solution was changed to 0.014 mL, and the amount of the EDC was changed to 0.025 mL, to obtain biodegradable film 4 and acetonitrile-containing film 4.

Biodegradable film 4 and acetonitrile-containing film 4 were evaluated in the same manner as in Example 1. The results are shown in Table 1.

As shown in Table 1, biodegradable film 4 had a high residual weight ratio, a high compressive load, and a high recovery rate. Acetonitrile-containing film 4 had a high complex elastic modulus.

Example 5

The same operation as in Example 1 was carried out except that 0.295 mL of solution 1 was changed to 0.223 mL of solution 5, 0.444 mL of solution 2 was changed to 0.517 mL of solution 6, 0.261 mL of solution 3 was changed to 0.260 mL of solution 7, the amount of DMAP solution was changed to 0.014 mL, and the amount of EDC was changed to 0.024 mL, to obtain biodegradable film 5 and acetonitrile-containing film 5.

Biodegradable film 5 and acetonitrile-containing film 5 were evaluated in the same manner as in Example 1. The results are shown in Table 1.

As shown in Table 1, biodegradable film 5 had a high residual weight ratio, a high compressive load, and a high recovery rate. Acetonitrile-containing film 5 had a high complex elastic modulus.

Example 6

The same operation as in Example 1 was carried out except that 0.295 mL of solution 1 was changed to 0.147 mL of solution 5, 0.444 mL of solution 2 was changed to 0.511 mL of solution 6, 0.261 mL of solution 3 was changed to 0.342 mL of solution 7, the amount of DMAP solution was changed to 0.014 mL, and the amount of EDC was changed to 0.024 mL, to obtain biodegradable film 6 and acetonitrile-containing film 6.

Biodegradable film 6 and acetonitrile-containing film 6 were evaluated in the same manner as in Example 1. The results are shown in Table 1.

As shown in Table 1, biodegradable film 6 had a high residual weight ratio, a high compressive load, and a high recovery rate. Acetonitrile-containing film 6 had a high complex elastic modulus.

Example 7

The same operation as in Example 1 was carried out except that 0.295 mL of solution 1 was changed to 0.063 mL of solution 5, 0.444 mL of solution 2 was changed to 0.201 mL of solution 6, 0.261 mL of solution 3 was changed to 0.736 mL of solution 7, the amount of DMAP solution was changed to 0.005 mL, the amount of EDC was changed to 0.010 mL, to obtain biodegradable film 7 and acetonitrile-containing film 7.

Biodegradable film 7 and acetonitrile-containing film 7 were evaluated in the same manner as in Example 1. The results are shown in Table 1.

As shown in Table 1, biodegradable film 7 had a high residual weight ratio, a high compressive load, and a high recovery rate. Acetonitrile-containing film 7 had a high complex elastic modulus.

Example 8

The same operation as in Example 1 was carried out except that 10.0 g of branched polymer a1 was changed to 8-branched PEG (SUNBRIGHT (registered trademark) HGEO20000; manufactured by NiGK Corporation) to obtain purified multivalent compound A3. The weight average molecular weight of the purified multivalent compound A3 as measured by GPC method was 32,000. The same operation as in Example 1 was carried out except that 10.0 g of branched polymer b1 was changed to 8-branched PEG (SUNBRIGHT (registered trademark) HGEO20000; manufactured by NiGK Corporation) to obtain purified multivalent compound B3. The weight average molecular weight of the purified multivalent compound B3 as measured by GPC method was 20,800. The same operation as in Example 1 was carried out except that 10.0 g of branched polymer c1 was changed to 8-branched PEG (SUNBRIGHT (registered trademark) HGEO20000; manufactured by NiGK Corporation) to obtain purified compound C3. The weight average molecular weight of the purified compound C3 as measured by GPC method was 33,000.

The same operation as in Example 1 was carried out except that purified multivalent compound A1 was changed to purified multivalent compound A3 to obtain solution 8. The same operation as in Example 1 was carried out except that purified multivalent compound B1 was changed to purified multivalent compound B3 to obtain solution 9. The same operation as in Example 1 was carried out except that purified compound C1 was changed to purified compound C3 to obtain solution 10.

The same operation as in Example 1 was carried out except that 0.295 mL of solution 1 was changed to 0.216 mL of solution 8, 0.444 mL of solution 2 was changed to 0.561 mL of solution 9, 0.261 mL of solution 3 was changed to 0.223 mL of solution 10, the amount of DMAP solution was changed to 0.008 mL, the amount of EDC was changed to 0.014 mL, to obtain biodegradable film 8 and acetonitrile-containing film 8.

Biodegradable film 8 and acetonitrile-containing film 8 were evaluated in the same manner as in Example 1. The results are shown in Table 1.

As shown in Table 1, biodegradable film 8 had a high residual weight ratio, a high compressive load, and a high recovery rate. Acetonitrile-containing film 8 had a high complex elastic modulus.

Example 9

The same operation as in Example 1 was carried out except that 10.0 g of branched polymer a1 was changed to 4-branched PEG (SUNBRIGHT (registered trademark) PTE20000; manufactured by NiGK Corporation) to obtain purified multivalent compound A4. The weight average molecular weight of the purified multivalent compound A4 as measured by GPC method was 34,200. The same operation as in Example 1 was carried out except that 10.0 g of branched polymer b1 was changed to 4-branched PEG (SUNBRIGHT (registered trademark) PTE20000; manufactured by NiGK Corporation) to obtain purified multivalent compound B4. The weight average molecular weight of the purified multivalent compound B4 as measured by GPC method was 20,400. The same operation as in Example 1 was carried out except that 10.0 g of branched polymer c1 was changed to 8-branched PEG (SUNBRIGHT (registered trademark) HGEO20000; manufactured by NiGK Corporation) to obtain purified compound C4. The weight average molecular weight of the purified compound C4 as measured by GPC method was 34,700.

The same operation as in Example 1 was carried out except that purified multivalent compound A1 was changed to purified multivalent compound A4 to obtain solution 11. The same operation as in Example 1 was carried out except that purified multivalent compound B1 was changed to purified multivalent compound B4 to obtain solution 12. The same operation as in Example 1 was carried out except that purified compound C1 was changed to purified compound C4 to obtain solution 13.

The same operation as in Example 1 was carried out except that 0.295 mL of solution 1 was changed to 0.227 mL of solution 11, 0.444 mL of solution 2 was changed to 0.542 mL of solution 12, 0.261 mL of solution 3 was changed to 0.231 mL of solution 13, the amount of DMAP solution was changed to 0.008 mL, the amount of EDC was changed to 0.014 mL, to obtain biodegradable film 9 and acetonitrile-containing film 9.

Biodegradable film 9 and acetonitrile-containing film 9 were evaluated in the same manner as in Example 1. The results are shown in Table 1.

As shown in Table 1, biodegradable film 9 had a high residual weight ratio, a high compressive load, and a high recovery rate. Acetonitrile-containing film 9 had a high complex elastic modulus.

Example 10

The same operation as in Example 1 was carried out except that 22.0 g of lactide was changed to 30.0 g of glycolide (PURASORB G; manufactured by PURAC BIOMATERIALS), and the amount of tin octylate solution was changed to 1.28 mL to obtain multivalent compound A5. The weight average molecular weight of the multivalent compound A5 as measured by GPC method was 14,100. The same operation as in Example 1 was carried out except that purified multivalent compound A1 was changed to purified multivalent compound A5 to obtain solution 14.

The same operation as in Example 1 was carried out except that 0.295 mL of solution 1 was changed to 0.277 mL of solution 14, the amount of solution 2 was changed to 0.456 mL, the amount of solution 3 was changed to 0.267 mL, the amount of DMAP solution was changed to 0.023 mL, the amount of EDC was changed to 0.040 mL, to obtain biodegradable film 10 and acetonitrile-containing film 10.

Biodegradable film 10 and acetonitrile-containing film 10 were evaluated in the same manner as in Example 1. The results are shown in Table 1.

As shown in Table 1, biodegradable film 10 had a high residual weight ratio, a high compressive load, and a high recovery rate. Acetonitrile-containing film 10 had a high complex elastic modulus.

Example 11

The same operation as in Example 1 was carried out except that anhydrous maleic acid (manufactured by Wako Pure Chemical Industries, Ltd.) was used instead of polycarboxylic acid b2 to obtain purified multivalent compound B5. The weight average molecular weight of the purified multivalent compound B14 as measured by GPC method was 5,800. The same operation as in Example 1 was carried out except that purified multivalent compound B2 was changed to purified multivalent compound B5 to obtain solution 15.

The same operation as in Example 1 was carried out except that 0.444 mL of solution 2 was changed to 0.444 mL of solution 15 to obtain biodegradable film 11 and acetonitrile-containing film 11.

Biodegradable film 11 and acetonitrile-containing film 11 were evaluated in the same manner as in Example 1. The results are shown in Table 1.

As shown in Table 1, biodegradable film 11 had a high residual weight ratio, a high compressive load, and a high recovery rate. Acetonitrile-containing film 11 had a high complex elastic modulus.

Comparative Example 1

The same operation as in Example 1 was carried out except that solution 3 was not used, and that 0.295 mL of solution 1 was changed to 0.463 mL of solution 5, 0.444 mL of solution 2 was changed to 0.537 mL of solution 6, the amount of DMAP solution was changed to 0.015 mL, the amount of EDC was changed to 0.025 mL, to obtain biodegradable film 12 and acetonitrile-containing film 12.

Biodegradable film 12 and acetonitrile-containing film 12 were evaluated in the same manner as in Example 1. The results are shown in Table 1.

As shown in Table 1, biodegradable film 12 had a high compressive load and a high recovery rate, but its residual weight ratio was low. Acetonitrile-containing film 12 had a high complex elastic modulus.

Comparative Example 2

The same operation as in Example 1 was carried out except that solution 3 was not used, and that 0.295 mL of solution 1 was changed to 0.435 mL of solution 8, 0.444 mL of solution 2 was changed to 0.565 mL of solution 9, the amount of DMAP solution was changed to 0.008 mL, the amount of EDC was changed to 0.014 mL, to obtain biodegradable film 13 and acetonitrile-containing film 13.

Biodegradable film 13 and acetonitrile-containing film 13 were evaluated in the same manner as in Example 1. The results are shown in Table 1.

As shown in Table 1, biodegradable film 13 had a high compressive load and a high recovery rate, but its residual weight ratio was low. Acetonitrile-containing film 13 had a high complex elastic modulus.

TABLE 1

| | Multivalent compound A | | | Multivalent compound B | | | Compound C | | |
|---|---|---|---|---|---|---|---|---|---|
| | Branched polymer a1 (PEG) | | Hydroxy-carboxylic acid a2 | Branched polymer b1 (PEG) | | Poly-carboxylic acid b2 | Branched polymer c1 (PEG) | | Hydroxy-carboxylic acid c2 |
| | Degree of branching | Average molecular weight | | Degree of branching | Average molecular weight | | Degree of branching | Average molecular weight | |
| Example 1 | 8 | 5000 | PLA | 8 | 5000 | succinic acid | 8 | 5000 | PCL |
| Example 2 | 8 | 5000 | PLA | 8 | 5000 | succinic acid | 8 | 5000 | PCL |
| Example 3 | 8 | 5000 | — | 8 | 5000 | succinic acid | 8 | 5000 | PCL |
| Example 4 | 8 | 10000 | PLA | 8 | 10000 | succinic acid | 8 | 10000 | PCL |
| Example 5 | 8 | 10000 | PLA | 8 | 10000 | succinic acid | 8 | 10000 | PCL |
| Example 6 | 8 | 10000 | PLA | 8 | 10000 | succinic acid | 8 | 10000 | PCL |
| Example 7 | 8 | 10000 | PLA | 8 | 10000 | succinic acid | 8 | 10000 | PCL |
| Example 8 | 8 | 20000 | PLA | 8 | 20000 | succinic acid | 8 | 20000 | PCL |
| Example 9 | 4 | 20000 | PLA | 4 | 20000 | succinic acid | 4 | 20000 | PCL |
| Example 10 | 8 | 5000 | PLA | 8 | 5000 | succinic acid | 8 | 5000 | PCL |
| Example 11 | 8 | 5000 | PLA | 8 | 5000 | maleic acid | 8 | 5000 | PCL |
| Comparative Example 1 | 8 | 10000 | PLA | 8 | 10000 | succinic acid | — | — | — |
| Comparative Example 2 | 8 | 20000 | PLA | 8 | 20000 | succinic acid | — | — | — |

| | Weight ratio * [% by weight] | Compressive load [mN] | Residual weight ratio [% by weight] | Complex elastic modulus [kPa] | Recovery rate [%] |
|---|---|---|---|---|---|
| Example 1 | 26 | 34 | 64 | 116 | 86 |
| Example 2 | 35 | 31 | 74 | 110 | 85 |
| Example 3 | 33 | 29 | 60 | 99 | 87 |
| Example 4 | 5 | 24 | 7 | 99 | 77 |
| Example 5 | 26 | 30 | 52 | 115 | 79 |
| Example 6 | 34 | 27 | 62 | 103 | 80 |
| Example 7 | 74 | 10 | 96 | 58 | 71 |
| Example 8 | 22 | 59 | 62 | 265 | 84 |
| Example 9 | 23 | 15 | 57 | 53 | 77 |
| Example 10 | 27 | 38 | 55 | 130 | 81 |
| Example 11 | 26 | 33 | 63 | 110 | 84 |
| Comparative Example 1 | 0 | 25 | 0 | 113 | 73 |
| Comparative Example 2 | 0 | 59 | 0 | 267 | 80 |

INDUSTRIAL APPLICABILITY

The biodegradable material can be used in the field of medicine, in applications for vascular embolization, adhesion-prevention, wound dressing, hemostasis, urinary incontinence-prevention or the like.

The invention claimed is:

1. A biodegradable material which is a chemically cross-linked product of:
    a multivalent compound A having 3 or more functional groups X selected from the group consisting of hydroxyl group, thiol group and amino group;
    a multivalent compound B having 3 or more functional groups Y selected from the group consisting of carboxyl group, isocyanate group and thioisocyanate group; and
    a compound C which is a copolymer of a hydroxycarboxylic acid(s) and a monomer(s) of a water-soluble polymer(s) selected from the group consisting of polyethylene glycol, polypropylene glycol, polyvinyl alcohol, polyhydroxyethyl acrylate, polyhydroxyethyl methacylate, carboxymethyl cellulose, hydroxymethyl cellulose and hydroxyethyl cellulose,
    wherein the hydroxycarboxylic acid(s) is selected from a homopolymer formed by homopolymerization and has a glass transition point of −40° C. or lower, and
    wherein the compound C has a degree of branching of 5 to 16.

2. The biodegradable material according to claim 1, wherein the weight ratio of said structure originated from said compound C is 18 to 70% by weight.

3. The biodegradable material according to claim 1, wherein said multivalent compound A is one of a) to e):
    a) a homopolymer of a monomer(s) of a water-soluble polymer(s) selected from the group consisting of polyethylene glycol, polypropylene glycol, or, a homopolymer or a copolymer of a monomer(s) of a water-soluble polymer(s) selected from the group consisting of polyvinyl alcohol, polyhydroxyethyl acrylate, polyhydroxyethyl methacrylate, carboxymethyl cellulose, hydroxymethyl cellulose and hydroxyethyl cellulose;
    b) a copolymer of the monomer of said water-soluble polymer and a monomer(s) of a hydrophobic polymer(s) selected from the group consisting of vinyl acetate and vinyl caprolactam;
    c) a copolymer of the monomer of said water-soluble polymer and a hydroxycarboxylic acid(s) whose homopolymer(s) formed by homopolymerization has/have a glass transition point of −39° C. or higher;
    d) a branched polymer formed by binding all of hydroxyl groups of a polyol with a homopolymer or a copolymer of a monomer(s) of a water-soluble polymer(s) selected from the group consisting of polyethylene glycol and polypropylene glycol;

e) a copolymer of said branched polymer and a hydroxycarboxylic acid(s) whose homopolymer(s) formed by homopolymerization has/have a glass transition point of −39° C. or higher.

4. The biodegradable material according to claim 1, wherein said multivalent compound B is one of f) to i):
   f) a compound formed by binding a hydroxyl group(s) of a homopolymer of a monomer(s) of a water-soluble polymer(s) selected from the group consisting of polyethylene glycol, polypropylene glycol, or, a homopolymer or a copolymer of a monomer(s) of a water-soluble polymer(s) selected from the group consisting of polyvinyl alcohol, polyhydroxyethyl acrylate, polyhydroxyethyl methacrylate, carboxymethyl cellulose, hydroxymethyl cellulose and hydroxyethyl cellulose, with a polycarboxylic acid(s);
   g) a compound formed by binding a hydroxyl group(s) of a copolymer of the monomer of said water-soluble polymer and a hydroxycarboxylic acid(s) whose homopolymer(s) formed by homopolymerization has/have a glass transition point of −39° C. or higher, with a polycarboxylic acid(s);
   h) a compound formed by binding a hydroxyl group(s) of a branched polymer formed by binding all of hydroxyl groups of a polyol with a homopolymer or a copolymer of a monomer(s) of a water-soluble polymer(s) selected from the group consisting of polyethylene glycol and polypropylene glycol, with a polycarboxylic acid(s);
   i) a compound formed by binding a hydroxyl group(s) of a copolymer of said branched polymer and a hydroxycarboxylic acid(s) whose homopolymer(s) formed by homopolymerization has/have a glass transition point of −39° C. or higher, with a polycarboxylic acid(s).

5. The biodegradable material according to claim 1, wherein the hydroxycarboxylic acid of compound C is 6-hydroxycaproic acid.

6. The biodegradable material according to claim 3, wherein said polyol is selected from the group consisting of glycerin, polyglycerin and pentaerythritol.

7. The biodegradable material according to claim 3, wherein said hydroxycarboxylic acid(s) whose homopolymer(s) formed by homopolymerization has/have a glass transition point of −39° C. or higher is/are selected from the group consisting of glycolic acid, lactic acid, glyceric acid, hydroxybutyric acid, malic acid, tartaric acid, hydroxyvaleric acid and 3-hydroxyhexanoic acid.

8. The biodegradable material according to claim 4, wherein said polycarboxylic acid(s) is/are selected from the group consisting of oxalic acid, malonic acid, succinic acid, glutaric acid, adipic acid, pimelic acid, suberic acid, azelaic acid, sebacic acid, malic acid, tartaric acid and fumaric acid.

9. A vascular embolization material comprising said biodegradable material according to claim 1.

10. An anti-adhesive material comprising said biodegradable material according to claim 1.

11. A wound dressing material comprising said biodegradable material according to claim 1.

12. A hemostatic material comprising said biodegradable material according to claim 1.

13. A urinary incontinence-preventing material comprising said biodegradable material according to claim 1.

14. A process of producing a biodegradable material comprising a chemical cross-linking step wherein a multivalent compound A having 3 or more functional groups X selected from the group consisting of hydroxyl group, thiol group and amino group, a multivalent compound B having 3 or more functional groups Y selected from the group consisting of carboxyl group, isocyanate group and thioisocyanate group, and a compound C which is a copolymer of a monomer(s) of a water-soluble polymer(s) selected from the group consisting of polyethylene glycol, polypropylene glycol, polyvinyl alcohol, polyhydroxyethyl acrylate, polyhydroxyethyl methacrylate, carboxymethyl cellulose, hydroxymethyl cellulose and hydroxyethyl cellulose, and a hydroxycarboxylic acid(s) whose homopolymer formed by homopolymerization has a glass transition point of −40° C. or lower, the compound C having a degree of branching of 5 to 16, are dissolved in a solvent to allow chemical cross-linking reaction to proceed, to obtain said biodegradable material.

* * * * *